(12) United States Patent (10) Patent No.: US 8,457,741 B2
Brisben et al. (45) Date of Patent: Jun. 4, 2013

(54) ESTIMATION OF DEDICATED BIPOLAR PACING VECTOR THRESHOLD

(75) Inventors: Amy Jean Brisben, Saint Paul, MN (US); Aaron R. McCabe, Minneapolis, MN (US); Kevin John Stalsberg, White Bear Lake, MN (US); Jacob I. Laughner, St. Louis, MO (US); Clayton S. Foster, Andover, MN (US); David W. Yost, Brooklyn Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 121 days.

(21) Appl. No.: 12/906,849

(22) Filed: Oct. 18, 2010

(65) Prior Publication Data

US 2011/0098773 A1 Apr. 28, 2011

Related U.S. Application Data

(60) Provisional application No. 61/253,885, filed on Oct. 22, 2009.

(51) Int. Cl.
*A61N 1/368* (2006.01)

(52) U.S. Cl.
USPC .......................................................... 607/28

(58) Field of Classification Search
USPC .......................................................... 607/28
See application file for complete search history.

(56) References Cited

U.S. PATENT DOCUMENTS

| | | | |
|---|---|---|---|
| 6,076,015 A | 6/2000 | Hartley et al. | |
| 6,587,723 B1 | 7/2003 | Sloman | |
| 6,684,101 B2 | 1/2004 | Daum | |
| 6,760,624 B2 | 7/2004 | Anderson et al. | |
| 7,471,983 B2 | 12/2008 | Voegele et al. | |
| 7,509,170 B2 | 3/2009 | Zhang et al. | |
| 2002/0078968 A1 | 6/2002 | Spinelli et al. | |
| 2004/0116978 A1 | 6/2004 | Bradley | |
| 2007/0255329 A1 | 11/2007 | Bjorling | |
| 2008/0046019 A1 | 2/2008 | Sathaye et al. | |
| 2008/0071319 A1 | 3/2008 | Sathaye et al. | |

FOREIGN PATENT DOCUMENTS

| | | |
|---|---|---|
| EP | 1291038 A2 | 3/2003 |
| WO | WO-2011/049875 A1 | 4/2011 |

OTHER PUBLICATIONS

International Application Serial No. PCT/US2010/53066, International Search Report mailed Jan. 26, 2011, 5 pgs.
International Application Serial No. PCT/US2010/53066, Written Opinion mailed Jan. 26, 2011, 6 pgs.
International Application Serial No. PCT/US2010/053066, International Preliminary Report on Patentability mailed May 3, 2012, 7 pgs.
Goetze, S., et al., "Clinical Evaluation of Two Different Evoked Response Sensing Methods for Automatic Capture Detection in the Left Ventricle", PACE, vol. 30(7), (Jul. 2007), 865-873.

*Primary Examiner* — Kennedy Schaetzle
(74) *Attorney, Agent, or Firm* — Schwegman Lundberg & Woessner, P.A.

(57) ABSTRACT

Methods and devices are described that allow estimation of an electrostimulation capture threshold, such as a dedicated bipolar pacing vector threshold. In an example, an equal-energy assumption between first and second pacing vectors can be used to estimate an electrostimulation capture threshold of a second pacing vector from a measured electrostimulation capture threshold of the first pacing vector and impedances of the first and second pacing vectors. In an example, a relationship between first and second pacing vectors can be determined from measured data, and a parameter of the relationship can be used with a measurement of an electrostimulation capture threshold of the first pacing vector to estimate an electrostimulation capture threshold of the second pacing vector.

20 Claims, 4 Drawing Sheets

ESTIMATION OF DEDICATED BIPOLAR PACING VECTOR THRESHOLD

CLAIM OF PRIORITY

This application claims the benefit of priority under 35 U.S.C. §119(e) of Brisben et al., U.S. Provisional Patent Application Ser. No. 61/253,885, entitled "ESTIMATION OF DEDICATED BIPOLAR PACING VECTOR THRESHOLD", filed on Oct. 22, 2009, which is herein incorporated by reference in its entirety.

BACKGROUND

Cardiac rhythm management (CRM) devices can help assist heart function, such as by providing pacing electrostimulations to evoke responsive heart contractions, cardiac resynchronization therapy (CRT) electrostimulations to coordinate the spatial nature of a heart contraction of one or more heart chambers, antitachyarrhythmia pacing, cardioversion, or defibrillation shocks to interrupt a tachyarrhythmia. In order to "capture" heart tissue near an electrode delivering electrostimulation energy, evoking a responsive depolarization and heart contraction, the electrostimulation energy must exceed a threshold value, sometimes referred to as a capture threshold. After determining the capture threshold, electrostimulations can be delivered in excess of the capture threshold to capture the heart tissue—too much electrostimulation energy may not be the best for the heart, moreover, it can waste energy and shorten the useful life of the device.

Sathaye et al. U.S. Patent Publication No. 2008/0046019, filed Aug. 17, 2006, and published Feb. 21, 2008 discloses a CRM device that can be pectorally-implanted and coupled to the heart via intravascular leads (sometimes referred to as catheters). In an example, a first lead can extend from the superior vena cava (SVC) into the right atrium (RA), and then into the right ventricle (RV). It can include an RV apical tip electrode, a slightly more proximal RV ring electrode, a still slightly more proximal RV shock coil electrode, and an even more proximal RA or SVC shock coil electrode. In an example, a second lead can extend from the SVC into the RA, through a coronary sinus (CS) into the coronary vasculature, such as near a portion of a left ventricle (LV). In an example, this second CS/LV lead can include first and second electrodes, from which electrostimulation energies can be delivered.

Determining an electrostimulation capture threshold can involve varying the electrostimulation energy up or down until the onset or loss of capture is detected. Whether capture occurs can be determined by observing the "evoked response" intrinsic heart signal waveform, after delivering electrostimulation, in the region of the electrode where the electrostimulation is delivered, such as described in Sathaye et al., U.S. Patent Publication No. 2008/0071319, filed Sep. 14, 2006, and published on Mar. 20, 2008 (see, e.g., FIGS. 2A, 2B, 3A, 3B and accompanying description). In sensing the evoked response signal, it is helpful to use one or more different electrodes than the electrodes from which the electrostimulation energy was delivered. This is because delivering an electrostimulation can cause a "pacing artifact" that can mask the desired evoked response signal if the same electrodes are used for both delivering the electrostimulation and sensing the evoked response. This can be particularly problematic, for example, for a CS/LV lead that includes only two electrodes for delivering a "dedicated bipolar" electrostimulation between these two electrodes located in the coronary vasculature in the LV region for evoking a responsive LV heart contraction. If there are only two CS/LV electrodes for delivering the electrostimulation, such as in a dedicated bipolar configuration, the resulting significant pace artifact can complicate a local measure of the resulting evoked response. This can preclude determining a capture threshold under conditions of dedicated bipolar electrostimulation.

Sathaye et al. U.S. Patent Publication No. 2008/0046019 discloses an example of how to estimate a "dedicated bipolar" capture threshold between two CS/LV electrodes by measuring an "extended bipolar" capture threshold between an LV electrode and an RV electrode, and using this measured information to estimate the "dedicated bipolar" capture threshold.

OVERVIEW

Sathaye et al. has as its assumption that "the capture threshold current of two pacing vectors having a common electrode is assumed to be about equal." (See Sathaye et al., ¶ 0048.) From this fundamental assumption, Sathaye et al. derives the following relationship:

$$V_{th\text{-}ex} = (V_{th\text{-}in}/Z_{in}) * Z_{ex}$$

which relates a first capture threshold voltage $V_{th\text{-}in}$ to a second capture threshold voltage $V_{th\text{-}ex}$ by a ratio of a measured impedance $Z_{in}$ associated with the electrode configuration of the first capture threshold voltage to a measured impedance $Z_{ex}$ associated with the second capture threshold voltage.

The present inventors have recognized that it is also possible to assume an equal electrostimulation energy for two pacing vectors sharing a common electrode, from which the following different relationship can be derived (assuming equal electrostimulation pulsewidths for both vectors):

$$V_{est} = (Z_{est}/Z_{meas})^{1/2} * V_{meas}$$

which relates a first measured capture threshold voltage $V_{meas}$ to an estimated second capture threshold voltage $V_{est}$ by a square root of a ratio of a measured impedance $Z_{est}$ associated with the electrode configuration of the estimated second capture threshold voltage $V_{est}$ to a measured impedance $Z_{meas}$ associated with the first measured capture threshold voltage. In an example, this relationship can be used to estimate a "dedicated bipolar" capture threshold voltage from a measured "extended bipolar" or unipolar capture threshold voltage and the measured impedances associated with these respective different electrode configurations.

As explained in detail below, the present inventors have recognized, among other things, that, in an example, a relationship (such as a linear fit or other regression) can be made between (1) first electrostimulation capture thresholds associated with a first electrode associated with a left ventricle and at least one other electrode that is located other than in association with the left ventricle (e.g., an "extended bipolar" or unipolar electrode configuration) and second electrostimulation capture thresholds associated with the first electrode and with a second electrode that is also associated with the left ventricle (e.g., a "dedicated bipolar" electrode configuration). Then, a first electrostimulation capture associated with a first electrode associated with a left ventricle of a subject and at least one other electrode that is located other than in association with the left ventricle of the subject (e.g., an "extended bipolar" or unipolar electrode configuration) can be measured and used together with a parameter of the relationship to determine a second electrostimulation capture threshold associated with the first electrode associated with the left ventricle of the subject and a second electrode that is also associated with the left ventricle of the subject (e.g., a "dedicated bipolar" electrode configuration).

Example 1 can include a capture threshold circuit, configured to measure a first electrostimulation capture threshold corresponding to a first vector between first and second electrodes. An impedance determination circuit can be configured to determine at least a first impedance associated with the first vector between the first and second electrodes and a second impedance associated with a second vector between the first electrode and a further third electrode. A processor circuit can be configured to estimate a second electrostimulation capture threshold corresponding to the second vector between the first electrode and the third electrode. The estimating can include scaling the first electrostimulation capture threshold by a scaling factor that is obtained using an equal energy assumption for the first and second vectors.

In Example 2, the subject matter of Example 1 can optionally be configured for performing the estimating to include scaling the first electrostimulation capture threshold by a scaling factor that is substantially proportional to a square root of a ratio of the second impedance to the first impedance.

In Example 3, the subject matter of any one of Examples 1 or 2 can optionally further comprise the first, second, and third electrodes.

In Example 4, the subject matter of any one of Examples 1-3 can be optionally configured such that the scaling factor is substantially proportional to a square root of a ratio of an electrostimulation duration, used with the first vector between first and second electrodes, and an electrostimulation duration, to be used with the second vector between the first and third electrodes.

In Example 5, the subject matter of any one of Examples 1-4 can be optionally configured such that the capture threshold circuit is further configured to measure the first electrostimulation capture threshold by taking the first vector between the first electrode located in association with a first heart chamber of a heart and the second electrode located elsewhere.

In Example 6, the subject matter of any one of Examples 1-5, can be optionally configured such that the first vector uses at least one of a second electrode located in association with a heart chamber across a septal region of the heart from the first electrode or a second electrode located in the body and outside of and not touching the heart.

In Example 7, the subject matter of any one of Examples 1-6 can be optionally configured such that the second vector is between the first electrode and the third electrode, wherein the third electrode is located in association with the first heart chamber of the heart.

In Example 8, the subject matter of any one of Examples 1-7 can optionally be configured such that the first and third electrodes are located intravascularly in association with a left ventricle of a heart.

In Example 9, the subject matter of any one of Examples 1-8 can optionally be configured such that the first electrode is configured as a cathode for delivering an electrostimulation for measuring a first electrostimulation capture threshold corresponding to the first vector.

In Example 10, the subject matter of any one of Examples 1-9 can optionally be configured such that the first electrode is also configured as a cathode for delivering an electrostimulation, using the second vector, exceeding the estimated second electrostimulation capture threshold.

In Example 11, the subject matter of any one of Examples 1-10 can optionally comprise measuring a first electrostimulation capture threshold corresponding to a first vector between first and second electrodes, determining a first impedance associated with the first vector between the first and second electrodes, determining a second impedance associated with a second vector between the first electrode and a further third electrode, and estimating a second electrostimulation capture threshold corresponding to the second vector between the first electrode and the further third electrode. The estimating can include scaling the first electrostimulation capture threshold by a scaling factor that that is obtained using an equal energy assumption for the first and second vectors.

In Example 12, the subject matter of any one of Examples 1-11 can optionally be configured such that the estimating includes scaling the first electrostimulation capture threshold by a scaling factor that is substantially proportional to a square root of a ratio of the second impedance to the first impedance.

In Example 13, the subject matter of any one of Examples 1-12 can optionally be configured such that the scaling factor is substantially proportional to a square root of a ratio of an electrostimulation duration used with the first vector between first and second electrodes to an electrostimulation duration to be used with the second vector between the first and third electrodes.

In Example 14, the subject matter of any one of Examples 1-13 can optionally be configured such that the measuring the first electrostimulation capture threshold corresponding to the first vector between the first and second electrodes comprises taking the first vector between the first electrode located in association with a first heart chamber of a heart and the second electrode located elsewhere.

In Example 15, the subject matter of any one of Examples 1-14 can optionally comprise taking the first vector using at least one of a second electrode located in association with a heart chamber across a septal region of the heart from the first electrode or a second electrode located in the body and outside of and not touching the heart.

In Example 16, the subject matter of any one of Examples 1-15 can optionally comprise taking the second vector between the first electrode and the third electrode, wherein the third electrode is located in association with the first heart chamber of the heart.

In Example 17, the subject matter of any one of Examples 1-16 can optionally be configured such that the first and third electrodes are located intravascularly in association with the left ventricle of the heart.

In Example 18, the subject matter of any one of Examples 1-17 can optionally be configured such that the first electrode is configured as a cathode for delivering an electrostimulation for measuring a first electrostimulation capture threshold corresponding to the first vector.

In Example 19, the subject matter of any one of Examples 1-18 can optionally be configured such that the first electrode is also configured as a cathode for delivering an electrostimulation, using the second vector, exceeding the estimated second electrostimulation capture threshold.

In Example 20, the subject matter of any one of Examples 1-18 can optionally comprise a capture threshold circuit, configured to measure a first electrostimulation capture threshold corresponding to a first vector between first and second electrodes, wherein the first electrode is located in association with a first heart chamber of a heart and the second electrode is located elsewhere. An impedance determination circuit can be configured to determine at least a first impedance associated with the first vector between the first and second electrodes and a second impedance associated with a second vector between the first electrode and a further third electrode. The third electrode can be located in association with the first heart chamber of the heart. A processor circuit can be configured to estimate a second electrostimulation capture threshold corresponding to the second vector between the first electrode and the further third electrode. The estimating can include scaling the first electrostimulation capture threshold by a scaling factor that is substantially proportional to a square root of a ratio of the second impedance to the first impedance and also substantially proportional to a square root of a ratio of an electrostimulation duration, used with the first vector between first and second electrodes, and an electrostimulation duration, to be used with the second vector between the first and third electrodes. The first and third electrodes can be located intravascularly in association with a left ventricle of a heart. The first electrode can be configured as a cathode for delivering an electrostimulation for measuring a first electrostimulation capture threshold corresponding to the first vector. The first electrode can also be configured as a cathode for delivering an electrostimulation, using the second vector, exceeding the estimated second electrostimulation capture threshold.

In Example 21, the subject matter of any one of Examples 1-20 can optionally comprise a processor circuit, which can be configured by performing instructions, to receive a parameter of a relationship between: (1) a plurality of first electrostimulation capture thresholds associated with a first electrode associated with a left ventricle and at least one other electrode that is located other than in association with the left ventricle, and (2) a plurality of second electrostimulation capture thresholds associated with the first electrode and with a second electrode that is also associated with the left ventricle. The processor circuit can be configured to receive a measured first electrostimulation capture threshold associated with a first electrode associated with a left ventricle of a subject and at least one other electrode that is located other than in association with the left ventricle of the subject. The processor circuit can be configured to use (1) the measured first electrostimulation capture threshold associated with the first electrode associated with the left ventricle of a subject and at least one other electrode that is located other than in association with the left ventricle of the subject, and (2) the parameter of the relationship, to determine a second electrostimulation capture threshold associated with the first electrode associated with the left ventricle of the subject and a second electrode that is also associated with the left ventricle of the subject. A pacing circuit can be coupled to the processor, and configured to deliver an electrostimulation to the subject, using the first and second electrodes associated with the left ventricle of the subject, at an electrostimulation energy exceeding the second electrostimulation capture threshold determined for the subject.

In Example 22, the subject matter of any one of Examples 1-21 can optionally be configured such that the relationship is determined from a population other than the subject.

In Example 23, the subject matter of any one of Examples 1-22 can optionally be configured such that the relationship is determined from a population other than the subject, wherein members of the population share a common characteristic including at least one of: a left ventricular lead location, a patient etiology, an electrostimulation pulsewidth, or a lead type.

In Example 24, the subject matter of any one of Examples 1-23 can optionally be configured such that the relationship is selected from multiple relationships determined corresponding to respective subpopulations of a population, the subpopulation sharing a common characteristic.

In Example 25, the subject matter of any one of Examples 1-24 can optionally be configured such that the relationship includes a linear fit, and wherein the parameter of the relationship includes a slope, and wherein the processor is configured to perform an instruction to scale, using the slope, the measured first electrostimulation capture threshold associated with the first electrode associated with the left ventricle of a subject and at least one other electrode that is located other than in association with the left ventricle of the subject to determine the second electrostimulation capture threshold associated with the first electrode associated with the left ventricle of the subject and the second electrode that is also associated with the left ventricle of the subject.

In Example 26, the subject matter of any one of Examples 1-25 can optionally be configured such that the parameter of the relationship includes an offset, and wherein the processor is configured to perform an instruction to shift, using the offset, the measured first electrostimulation capture threshold associated with the first electrode associated with the left ventricle of a subject and at least one other electrode that is located other than in association with the left ventricle of the subject to determine the second electrostimulation capture threshold associated with the first electrode associated with the left ventricle of the subject and the second electrode that is also associated with the left ventricle of the subject.

In Example 27, the subject matter of any one of Examples 1-26 can optionally be configured such that the other electrode is configured to be located in association with a heart chamber across a septal region of the heart from the first and second electrodes.

In Example 28, the subject matter of any one of Examples 1-27 can optionally be configured such that the other electrode is configured to be located in the body and outside of and not touching the heart.

In Example 29, the subject matter of any one of Examples 1-28 can optionally comprise receiving a parameter of a relationship between: (1) a plurality of first electrostimulation capture thresholds associated with a first electrode associated with a left ventricle and at least one other electrode that is located other than in association with the left ventricle, and (2) a plurality of second electrostimulation capture thresholds associated with the first electrode and with a second electrode that is also associated with the left ventricle. A measured first electrostimulation capture threshold can be received, associated with a first electrode associated with a left ventricle of a subject and at least one other electrode that is located other than in association with the left ventricle of the subject. The measured first electrostimulation capture threshold associated with the first electrode associated with the left ventricle of a subject and at least one other electrode that is located other than in association with the left ventricle of the subject, and the parameter of the relationship can be used to determine a second electrostimulation capture threshold associated with the first electrode associated with the left ventricle of the subject and a second electrode that is also associated with the left ventricle of the subject.

In Example 30, the subject matter of any one of Examples 1-29 can optionally be configured such that the relationship is determined from a population other than the subject.

In Example 31, the subject matter of any one of Examples 1-30 can optionally comprise determining the relationship from a population other than the subject.

In Example 32, the subject matter of any one of Examples 1-31 can optionally be configured such that the relationship is determined from a population other than the subject, wherein members of the population share a common characteristic including at least one of: a left ventricular lead location, a patient etiology, an electrostimulation pulsewidth, or a lead type.

In Example 33, the subject matter of any one of Examples 1-32 can optionally be configured such that the relationship is selected from multiple relationships determined corresponding to respective subpopulations of a population, the subpopulation sharing a common characteristic.

In Example 34, the subject matter of any one of Examples 1-33 can optionally be configured such that the parameter of the relationship includes a slope, and comprising scaling, using the slope, the measured first electrostimulation capture threshold associated with the first electrode associated with the left ventricle of a subject and at least one other electrode that is located other than in association with the left ventricle of the subject in determining the second electrostimulation capture threshold associated with the first electrode associated with the left ventricle of the subject and the second electrode that is also associated with the left ventricle of the subject.

In Example 35, the subject matter of any one of Examples 1-34 can optionally be configured such that the parameter of the relationship includes an offset, and comprising shifting, using the offset, the measured first electrostimulation capture threshold associated with the first electrode associated with the left ventricle of a subject and at least one other electrode that is located other than in association with the left ventricle of the subject in determining the second electrostimulation capture threshold associated with the first electrode associated with the left ventricle of the subject and the second electrode that is also associated with the left ventricle of the subject.

In Example 36, the subject matter of any one of Examples 1-35 can be optionally configured such that the other electrode is located in association with a heart chamber across a septal region of the heart from the first and second electrodes.

In Example 37, the subject matter of any one of Examples 1-36 can optionally be configured such that the other electrode is located in the body and outside of and not touching the heart.

In Example 38, the subject matter of any one of Examples 1-36 can optionally comprise a processor circuit, which can be configured by performing instructions. The processor circuit can receive a parameter of a regression relationship, determined from a population other than a subject, between: (1) a plurality of first electrostimulation capture thresholds associated with a first electrode associated with a left ventricle and at least one other electrode that is located other than in association with the left ventricle, and (2) a plurality of second electrostimulation capture thresholds associated with the first electrode and with a second electrode that is also associated with the left ventricle, and wherein the parameter of the regression relationship includes a slope and an offset. The processor circuit can receive a measured first electrostimulation capture threshold associated with a first electrode associated with a left ventricle of the subject and at least one other electrode that is located other than in association with the left ventricle of the subject. The processor circuit can scale, using the slope, and shift, using the offset, the measured first electrostimulation capture threshold associated with the first electrode associated with the left ventricle of a subject and at least one other electrode that is located other than in association with the left ventricle of the subject, to determine a second electrostimulation capture threshold associated with the first electrode associated with the left ventricle of the subject and a second electrode that is also associated with the left ventricle of the subject. A pacing circuit can be coupled to the processor and configured to deliver an electrostimulation to the subject, using the first and second electrodes associated with the left ventricle of the subject, at an electrostimulation energy exceeding the second electrostimulation capture threshold determined for the subject. The other electrode can be configured to be located at least one of: (1) in association with a heart chamber across a septal region of the heart from the first and second electrodes, or (2) in the body and outside of and not touching the heart.

In Example 39, the subject matter of any one of Examples 1-38 can optionally further comprise the first and second electrodes and the other electrode that is located other than in association with the left ventricle. The first electrode can be configured to be cathodic both in the subject and in the population other than the subject.

These examples can be combined with each other, or with other subject matter described herein. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
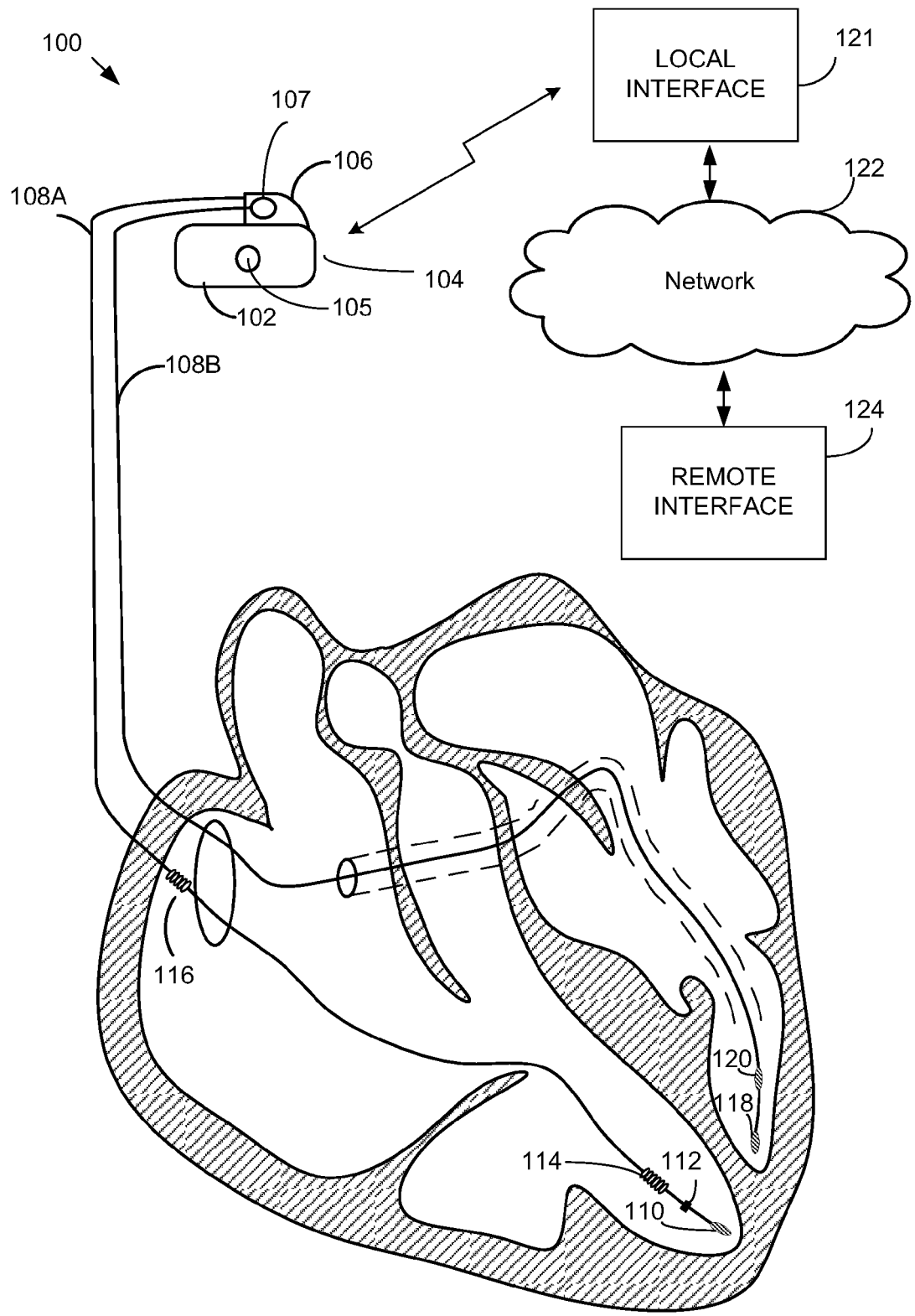
FIG. 1 shows an example of an implantable or other ambulatory cardiac rhythm management (CRM) device.

FIG. 1 shows an example of an implantable or other ambulatory cardiac rhythm management (CRM) device 100. In an example, the CRM device 100 can include an electronics unit 102 that can include a hermetically-sealed biocompatible housing 104 and a header 106 extending therefrom. The housing 104 can carry a power source and electronics. The header 106 can include one or more receptacles, such as for receiving the proximal ends of intravascular leads 108A-B. In an example, the lead 108A can be an intravascular RV lead that can extend from the superior vena cava (SVC) into the right atrium (RA), and then into the right ventricle (RV). The lead 108A can include an RV apical tip electrode 110, a slightly more proximal RV ring electrode 112, a still slightly more proximal RV shock coil electrode 114, and an even more proximal RA or SVC shock coil electrode 116. The various electrodes can be used for delivering electrical energy or sensing intrinsic electrical heart signals. The intravascular CS/LV lead 108B can extend from the SVC into the RA, through a coronary sinus (CS) into the coronary vasculature, such as near a portion of a left ventricle (LV). In an example, this second CS/LV lead 108B can include a distal electrode 118 and a proximal electrode 120, from which electrostimulation energies can be delivered or intrinsic electrical heart signals can be sensed. Other electrodes (e.g., a housing electrode 105 on the housing 104, a header electrode 107 on the header 106, an epicardial electrode, a subcutaneous electrode located away from the heart, or an electrode located elsewhere) or leads (e.g., right atrial) can be used.

In an example, an implantable CRM device 100 can include a communication circuit, such as to wireless communicate unidirectionally or bidirectionally with an external local interface 121, such as a CRM device programmer, repeater, handheld device, or the like. The local interface 121 can be configured to communicate via a wired or wireless computer or communication network 122 to a remote interface 124, such as a remote computer or server or the like.

Figure 2:
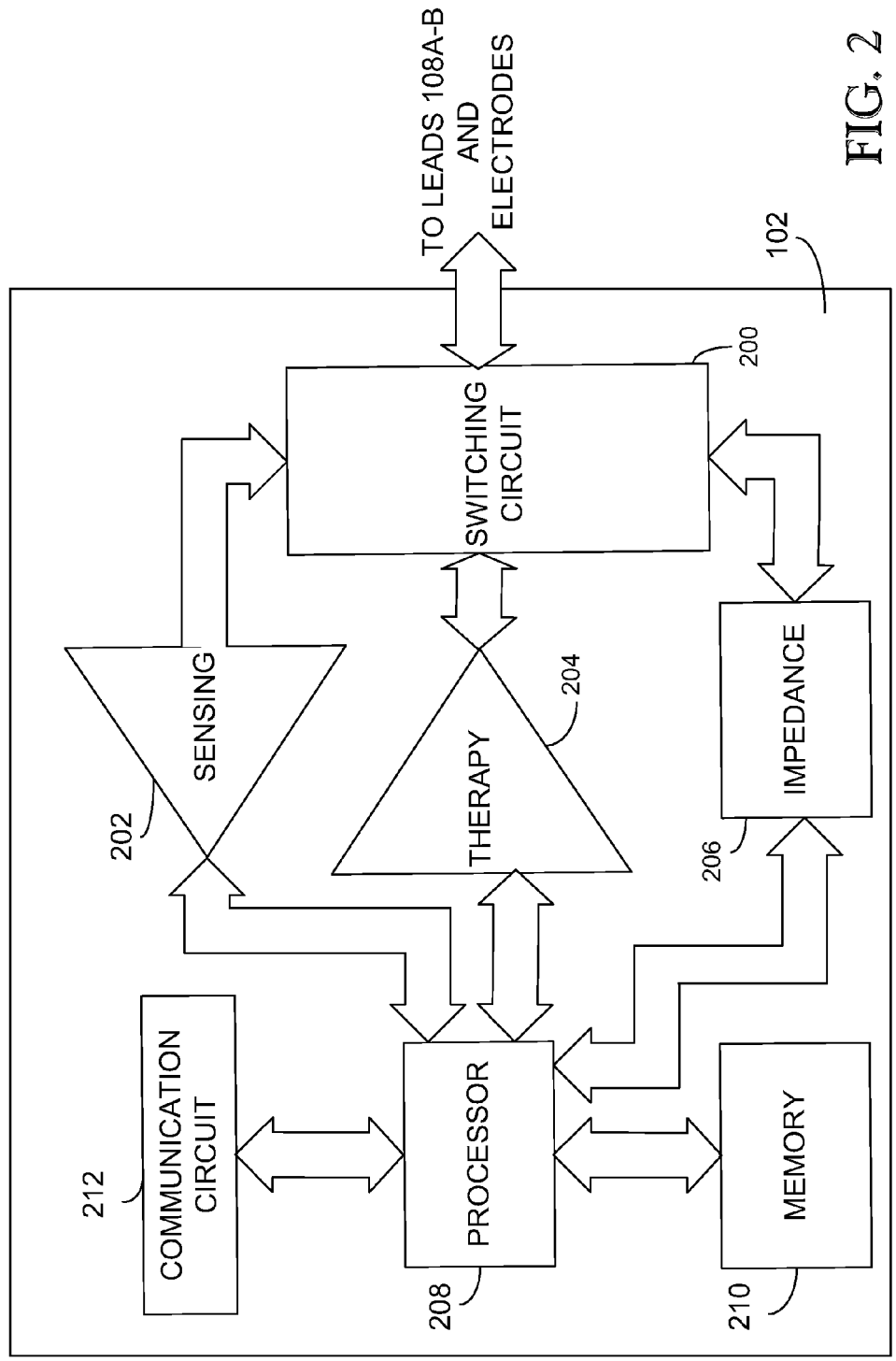
FIG. 2 shows an example of portions of a CRM device electronics unit.

FIG. 2 shows an example of portions of the CRM device electronics unit 102. In an example, this can include a switching circuit 200, such as for selectively connecting to the various electrodes such as on the leads 108A-B or elsewhere. A sensing circuit 202 can be selectively coupled to various electrodes by the switching circuit 200, and can include sense amplifiers, filter circuits, other circuits such as for sensing intrinsic electrical signals, such as intrinsic heart signals. A therapy circuit 204 can be selectively coupled to various electrodes by the switching circuit 200, and can include therapy energy generation circuitry (e.g., capacitive, inductive, or other) such as for generating, storing, or delivering an electrostimulation, cardioversion, defibrillation, or other energy. An impedance measurement circuit 206 can be selectively coupled to various electrodes by the switching circuit 200, such as for measuring a lead impedance, a tissue impedance, a regional or organ impedance, or other impedance. In an example, the sensing circuit 202, the therapy circuit 204, or the impedance circuit 206 can be coupled to a processor circuit 208.

In an example, the processor 208 can perform instructions, such as for signal processing of signals derived by the sensing circuit 202 or the impedance circuit 206, or for controlling operation of the therapy circuit 204 or other operations of the CRM device 100. The processor 208 can also be coupled to or include a memory circuit 210, such as for storing or retrieving instructions or data, or a communication circuit 212, such as for communicating with the local interface 121.

In an example, the processor 208 can be configured for estimating a capture threshold, such as for a "dedicated bipolar" configuration delivering electrostimulations between electrodes 118 and 120, both of which are located in association with the LV, such as in the coronary vasculature associated with the LV. Such estimation can include using a measured capture threshold for an electrode configuration including at least one electrode that is not associated with the LV—as an illustrative example, an "extended bipolar" configuration, such as for delivering electrostimulations between electrodes 118 and 112. In this illustrative example, the electrode 118 can serve as a cathode for both the "dedicated bipolar" configuration and the "extended bipolar" configuration.

As discussed above, Sathaye et al. U.S. Patent Publication No. 2008/0046019 discloses an example of how to estimate a "dedicated bipolar" capture threshold between two CS/LV electrodes by measuring an "extended bipolar" capture threshold between an LV electrode and an RV electrode, and using this measured information to estimate the "dedicated bipolar" capture threshold.

The present inventors have recognized, among other things, that although Sathaye et al. is certainly useful, its usefulness may be limited across the full range of capture thresholds, by its assumption that "the capture threshold current of two pacing vectors having a common electrode is assumed to be about equal." (See Sathaye et al., ¶ 0048.) From this fundamental assumption, Sathaye et al. derives the following relationship $$V_{th\text{-}ex} = (V_{th\text{-}in}/Z_{in})*Z_{ex},$$

which relates a first capture threshold voltage $V_{th\text{-}in}$ to a second capture threshold voltage $V_{th\text{-}ex}$ by a ratio of a measured impedance $Z_{in}$ associated with the electrode configuration of the first capture threshold voltage to a measured impedance $Z_{ex}$ associated with the second capture threshold voltage. The present inventors have recognized, however, that the above relationship can have performance limitations within the full range of capture thresholds that are expected to be encountered.

As explained in detail below, the present inventors have recognized, among other things, that, in an example, it may be better to instead assume an equal electrostimulation energy for two pacing vectors sharing a common electrode. This can be expressed as:

$$((V_{meas})^2/Z_{meas})*t_{meas} = ((V_{est})^2/Z_{est})*t_{est}),$$

where $V_{meas}$ is the electrostimulation voltage amplitude of a first pacing vector, $Z_{meas}$ is the impedance associated with the first pacing vector, and $t_{meas}$ is the electrostimulation pulse duration of the first pacing vector, and where $V_{est}$ is the electrostimulation voltage amplitude of a second pacing vector, $Z_{est}$ is the impedance associated with the second pacing vector, and $t_{est}$ is the electrostimulation pulse duration of the second pacing vector. With this in mind, and assuming equal electrostimulation pulse durations, the following different relationship can be derived:

$$V_{est} = (Z_{est}/Z_{meas})^{1/2} * V_{meas}.$$

For different electrostimulation pulsewidths between the measured and estimated electrode configurations, this expression can be re-written as $$V_{est} = ((Z_{est}*t_{meas})/(Z_{meas}*t_{est}))^{1/2} * V_{meas}.$$

In an example, this relationship can be used to estimate a "dedicated bipolar" capture threshold voltage from a measured "extended bipolar" capture threshold voltage and the measured impedances associated with these respective different electrode configurations.

Figure 3:
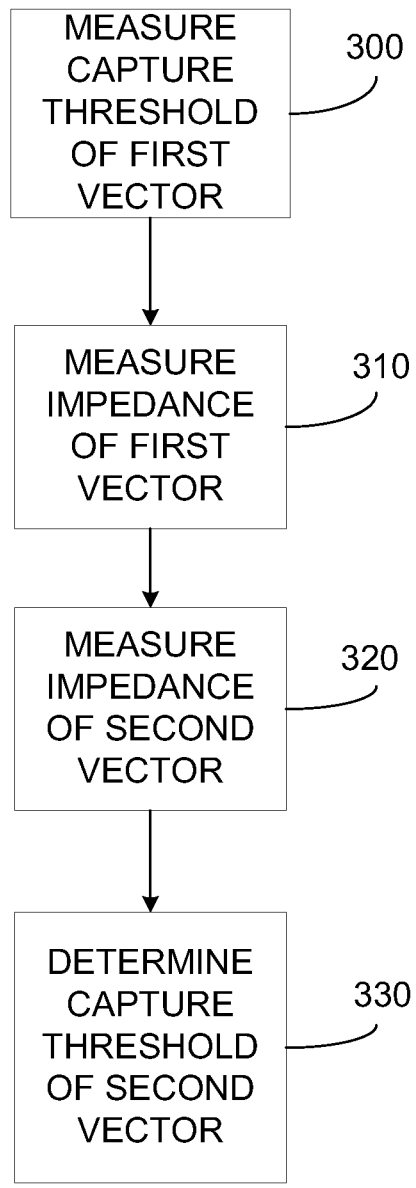
FIG. 3 shows an example of a process for estimating a capture threshold.

FIG. 3 shows an example of a process for estimating a capture threshold of a second pacing vector or configuration (e.g., dedicated bipolar) using information from one or more measurements about a measured capture threshold of a first pacing vector or configuration (e.g., extended bipolar or unipolar) along with a measured impedance associated with the second pacing vector or configuration (e.g., dedicated bipolar) and a measured impedance associated with the first pacing vector or configuration (e.g., extended bipolar or unipolar).

At 300, a capture threshold of a first pacing vector or configuration (e.g., extended bipolar or unipolar) can be directly measured. In an example, this can include delivering varying-energy electrostimulations in an extended bipolar configuration between a cathodic LV distal electrode 118 and an anodic RV ring electrode 112. Whether a resulting capture has been evoked in response to a particular electrostimulation can be determined, in an example, by then using the sensing circuit 202 and the switching circuit 200 to sense the responsive intrinsic electrical heart signal, such as using a unipolar sensing configuration between the LV proximal electrode 120 and the can electrode 105. The resulting sensed signal can then be signal-processed such as to determine whether an evoked response indicative of capture is present, such as described or incorporated by reference in Sathaye et al., U.S. Patent Publication No. 2008/0071319, filed Sep. 14, 2006, and published on Mar. 20, 2008, which is incorporated herein by reference in its entirety, including its description of capture determination. The processor 208 can then store in the memory 210 the resulting measured capture threshold voltage $V_{meas}$ associated with the extended bipolar first pacing configuration.

At 310, a first impedance $Z_{meas}$ associated with the first pacing vector or configuration (e.g., extended bipolar) can be measured. In an example, this can include measuring the impedance of an extended bipolar configuration between a cathodic LV distal electrode 118 and an anodic RV ring electrode 112. Examples of impedance measurement are described in commonly owned U.S. Pat. No. 6,076,015 and U.S. Pat. No. 6,760,620, each of which is incorporated herein by reference for its description of examples of impedance determination such as for an electrode configuration. The processor 208 can then store in the memory 210 the resulting measured first impedance $Z_{meas}$ associated with the extended bipolar first pacing configuration.

At 320, a measurement is made of a second impedance $Z_{est}$ associated with a second pacing vector (e.g., dedicated bipolar), such as sharing an electrode (e.g., preferably a cathode) with the first pacing vector (e.g., configured for delivering an electrostimulation using a cathodic LV distal electrode 118). In an example, in later use, this second pacing vector or configuration will deliver electrostimulations in excess of the estimated second capture threshold $V_{est}$ in a dedicated bipolar configuration between a cathodic LV distal electrode 118 and an anodic LV proximal electrode 120. Examples of impedance measurement are described in commonly owned U.S. Pat. No. 6,076,015 and U.S. Pat. No. 6,760,620, each of which is incorporated herein by reference for its description of examples of impedance determination such as for an electrode configuration. The processor 208 can then store in the memory 210 the resulting measured second impedance $Z_{est}$ associated with the dedicated bipolar second pacing configuration.

At 330, a second capture threshold $V_{est}$ of a second pacing vector or configuration (e.g., dedicated bipolar) can be determined. In an example, in later use, this second pacing vector or configuration will deliver electrostimulations in excess of the estimated second capture threshold $V_{est}$ in a dedicated bipolar configuration between a cathodic LV distal electrode 118 and an anodic LV proximal electrode 120. In an example, this determination can be an estimation performed by the processor 208, such as by using the $V_{meas}$, $Z_{meas}$, and $Z_{est}$ stored in the memory to compute $V_{est}$ such as according to:

$$V_{est} = ((Z_{est} * t_{meas})/(Z_{meas} * t_{est}))^{1/2} * V_{meas}$$

as described above, or if $t_{meas} = t_{est}$, according to:

$$V_{est} = ((Z_{est}/Z_{meas}))^{1/2} * V_{meas}$$

such as also described above. In both of these examples, the second capture threshold $V_{est}$ can be determined using a scaling factor that is proportional to the square root of the ratio of the second impedance $Z_{est}$ to the first impedance $Z_{meas}$. For clarity, the above description of FIG. 3 has been described with respect to a particular first pacing vector, a particular second pacing vector, and a particular evoked response sensing vector. However, the above-described technique can also be applied to other electrode configurations used as the first pacing vector, the second pacing vector, or the evoked response sensing vector, some illustrative examples of which are listed in Table 1, below, with the above-emphasized example repeated as configuration number 1 in Table 1 below.

TABLE 1

Some Illustrative Examples of Other Configurations

| Config. No. | First Pacing Vector (Cathode, Anode) | Second Pacing Vector (Cathode, Anode) | Evoked Response Capture Threshold Sensing Vector |
|---|---|---|---|
| 1 | (LV distal 118, RV coil 114) | (LV distal 118, LV proximal 120) | (LV proximal 120, housing 105) |
| 2 | (LV distal 118, housing 105) | (LV distal 118, LV proximal 120) | (LV proximal 120, housing 105) |
| 3 | (LV proximal 120, RV coil 114) | (LV distal 118, LV proximal 120) | (LV distal 118, housing 105) |
| 4 | (LV proximal 120, housing 105) | (LV distal 118, LV proximal 120) | (LV distal 118, housing 105) |
| 5 | (LV proximal 120, RV coil 114) | (LV proximal 120, LV distal 118) | (LV distal 118, housing 105) |
| 6 | (LV proximal 120, housing 105) | (LV proximal 120, LV distal 118) | (LV distal 118, housing 105) |
| 7 | (LV distal 118, RV coil 114) | (LV proximal 120, LV distal 118) | (LV proximal 120, housing 105) |
| 8 | (LV distal 118, housing 105) | (LV proximal 120, LV distal 118) | (LV proximal 120, housing 105) |

Other electrode configurations can also be used, as an example, the RV tip electrode 110 can be substituted for the RV ring electrode 112 in various of the configurations of Table 1. In another example, the RV ring electrode 112 can be substituted for the RV coil electrode 114 in various of the configurations of Table 1. In another example, the header electrode 107 can be substituted for the housing electrode 105 in various of the configurations of Table 1. Other variations, permutations, or combinations are also possible.

Our measured preclinical experimental data indicates that, for all electrode configurations tested, the error between the estimated second pacing threshold and an experimentally measured value of the second pacing threshold is less using the present technique, which assumes an equal electrostimulation energy for two pacing vectors sharing a common electrode, than for the technique described in Sathaye et al. U.S. Patent Publication No. 2008/0046019, which may be limited by its assumption that "the capture threshold current of two pacing vectors having a common electrode is assumed to be about equal." (See Sathaye et al., ¶ 0048.) Moreover, the present technique is more flexible, in that it allows different electrostimulation pulsewidths to be used with respective first and second pacing vectors, if desired.

Figure 4:
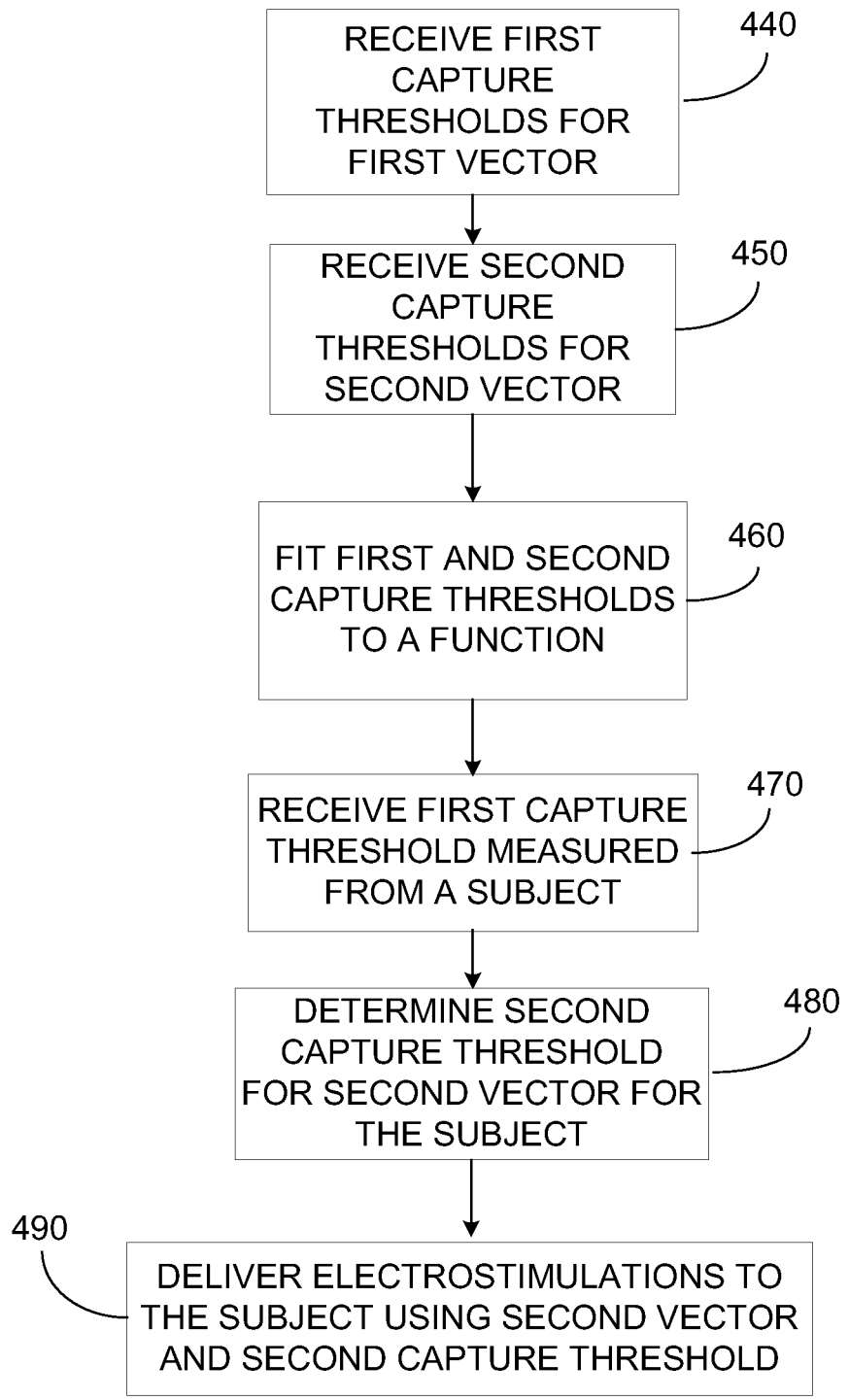
FIG. 4 shows an example of a process for estimating a capture threshold of a second pacing vector or configuration (e.g., dedicated bipolar) using information about a relationship (e.g., a linear fit or other regression or function) between (1) one or more measurements of a measured capture threshold of a first pacing vector or configuration (e.g., extended bipolar or unipolar) and (2) one or more measurements about a measured capture threshold of a second pacing vector or configuration (e.g., dedicated bipolar).

FIG. 4 shows an example of a process for estimating a capture threshold of a second pacing vector or configuration (e.g., dedicated bipolar) using information about a relationship (e.g., a linear fit or other regression or function) between (1) one or more measurements of a measured capture threshold of a first pacing vector or configuration (e.g., extended bipolar or unipolar) and (2) one or more measurements about a measured capture threshold of a second pacing vector or configuration (e.g., dedicated bipolar).

At 440, a plurality of first electrostimulation capture thresholds can be received. In an example, these first electrostimulation thresholds have been measured from a population of subjects using a first pacing vector or configuration with a first electrode located in a left ventricle (e.g., LV distal electrode 118 or LV proximal electrode 120) and a second electrode located elsewhere, such as across the septum in the right ventricle (e.g., RV ring electrode 112) or at a pectorally implanted electronics unit (e.g., housing electrode 105).

At 450, a plurality of second electrostimulation capture thresholds can be received. In an example, these second electrostimulation capture thresholds have been measured from a population using a second pacing vector or configuration with a first and second electrodes both located in association with the left ventricle (e.g., LV distal electrode 118 and LV proximal electrode 120).

In an example, a pair of first and second electrostimulation capture thresholds is obtained from a particular subject, and multiple such pairs are obtained from a population of subjects.

At 460, the pairs of first and second electrostimulation capture thresholds can be conceptualized as being plotted against each other on a graph with an x-axis representing magnitude of the first electrostimulation capture thresholds, and a y-axis representing magnitude of the corresponding second electrostimulation capture thresholds. In this way, the paired data can be fitted to a function, such as a linear fitting to a line, or another desired fitting to a higher-order function to represent the data or a relationship between the x-axis data and the y-axis data. For a linear fitting, the resulting best-fit line representing the data can, in turn, be represented as one or more parameters, such as by a slope (m) and/or an offset (b) such as in an equation for the line written as y=mx+b. The one or more parameters, such as the slope and/or the offset, obtained from the population, can later be used when a new subject is encountered, such as to estimate one of the first or second electrostimulation capture thresholds for the new subject using the other of the first or second electrostimulation capture thresholds and one or more of the parameters (e.g., slope and/or offset) from the population-derived fitted relationship.

Although the above description has emphasized the use of linear fitting to a line, in an example, the relationship between the x and y data can use least squares or other regression analysis, or other statistical or mathematical techniques for determining the relationship.

At 470, a measured first electrostimulation capture threshold from a subject is received. In an example, this is a measured first electrostimulation capture threshold using a first pacing vector or configuration (e.g., extended bipolar or unipolar) from a subject that was not included in the population from which fitted data was obtained.

At 480, a second electrostimulation capture threshold (e.g., dedicated bipolar) is determined for the subject from which the first electrostimulation capture threshold (e.g., extended bipolar or unipolar) was received. In an example, this includes using the measured value of the first electrostimulation capture threshold $V_{meas}$ and one or more parameters (e.g., slope (m) and/or offset (b)) of the population-derived fitted relationship (e.g., linear fit) to estimate the second electrostimulation capture threshold, such as according to:

$$V_{est} = m * V_{meas} + b$$

where $V_{est}$ is the estimated second electrostimulation capture threshold for the second pacing vector or configuration (e.g., dedicated bipolar), m is the slope parameter from the population-derived linear fit, $V_{meas}$ is the measured first electrostimulation capture threshold from the same subject for which the second electrostimulation capture threshold is being estimated, and b is the offset from the population-derived linear fit.

At 490, the estimated second electrostimulation capture threshold for the second pacing vector or configuration (e.g., dedicated bipolar) can be used by the CRM device 100, such as for delivering electrostimulations to the subject using the second pacing vector or configuration at an electrostimulation energy that exceeds the estimated second electrostimulation capture threshold.

In the above description with respect to FIG. 4, the linear fitting of the population data typically will not be performed by the processor 208 of the CRM device 100, but instead can be performed by another processing device, such as by the remote interface 124, in an example. The communication circuit 212 of the CRM device 100 can receive the one or more parameters (e.g., slope (m) and/or offset (b)) of the population-derived fitted relationship (e.g., linear fit), which can be stored in the memory 210 and retrieved by the processor 208 for use in determining the second electrostimulation capture threshold.

In an example, the population-derived data can be split out into subpopulation-derived data, such as for a particular subpopulation sharing one or more characteristics. A linear fit or other best-fit function can be computed for each subpopulation, and a slope and/or offset or other parameter of one or more of these best-fit functions can be communicated to the CRM device 100. The CRM device 100 can then use the slope and/or offset of a particular sub-population, for example, which is deemed particularly well-suited to represent the patient with which the CRM device 100 is associated. Examples of a characteristic that can be used as a factor to define a sub-population can include, for example, a left ventricular lead location, a patient etiology, an electrostimulation pulsewidth, or a lead type.

In an example, the second electrostimulation capture threshold associated with the second pacing vector or configuration can be determined from measured first electrostimulation capture thresholds associated with N different first pacing vectors or configurations, such as according to:

$$V_{est} = \sum_{i=1}^{N} a_i * (m_{est-i} * V_{meas\_i} + b_{est\_i}),$$

in which $V_{est}$ is the estimated second electrostimulation capture threshold associated with the second pacing vector or configuration, $V_{meas\_i}$ is the measured first electrostimulation capture threshold associated with a particular one of the N different first pacing vectors or configurations, and $m_{est\_i}$ and $b_{est\_i}$ are the corresponding slope and offset parameters associated with population-derived linear fit data for the same corresponding first pacing vector or configuration, and $a_i$ is a weighting associated with the particular first pacing vector or configuration. In an example, one or more of the different first pacing vectors listed in Table 1 can be used in this manner to estimate one or more second electrostimulation capture thresholds.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   a capture threshold circuit, configured to measure a first electrostimulation capture threshold corresponding to a first vector having a first pulsewidth between first and second electrodes;
   an impedance determination circuit, configured to determine at least a first impedance associated with the first vector between the first and second electrodes and a second impedance associated with a second vector having a second pulsewidth between the first electrode and a further third electrode, wherein the second pulsewidth is different from the first pulsewidth; and
   a processor circuit, configured to estimate a second electrostimulation capture threshold corresponding to the second vector between the first electrode and the third electrode, the estimating including scaling the first electrostimulation capture threshold by a scaling factor that is obtained using an equal energy assumption for the first and second vectors.

2. The apparatus of claim 1, wherein the estimating includes scaling the first electrostimulation capture threshold by a scaling factor that is substantially proportional to a square root of a ratio of the second impedance to the first impedance.

3. The apparatus of claim 2, further comprising the first, second, and third electrodes.

4. The apparatus of claim 2, wherein the scaling factor is substantially proportional to a square root of a ratio of an electrostimulation duration, used with the first vector between first and second electrodes, and an electrostimulation duration, to be used with the second vector between the first and third electrodes.

5. The apparatus of claim 2, further comprising:
   the first, second, and third electrodes, wherein the capture threshold circuit is further configured to measure the first electrostimulation capture threshold by taking the first vector between the first electrode located in association with a first heart chamber of a heart and the second electrode located elsewhere.

6. The apparatus of claim 5, wherein the first vector uses at least one of a second electrode located in association with a heart chamber across a septal region of the heart from the first electrode or a second electrode located in the body and outside of and not touching the heart.

7. The apparatus of claim 2, further comprising:
   the first, second, and third electrodes, wherein the second vector is between the first electrode and the third electrode, wherein the third electrode is located in association with a first heart chamber of the heart.

8. The apparatus of claim 7, wherein the first and third electrodes are located intravascularly in association with a left ventricle of a heart.

9. The apparatus of claim 2, wherein the first electrode is configured as a cathode for delivering an electrostimulation for measuring a first electrostimulation capture threshold corresponding to the first vector.

10. The apparatus of claim 9, wherein the first electrode is also configured as a cathode for delivering an electrostimulation, using the second vector, exceeding the estimated second electrostimulation capture threshold.

11. A method comprising:
    measuring a first electrostimulation capture threshold corresponding to a first vector having a first pulsewidth between first and second electrodes;
    determining a first impedance associated with the first vector between the first and second electrodes;

determining a second impedance associated with a second vector having a second pulsewidth between the first electrode and a further third electrode wherein the second pulsewidth is different from the first pulsewidth; and estimating, using a processor circuit, a second electrostimulation capture threshold corresponding to the second vector between the first electrode and the further third electrode, the estimating including scaling the first electrostimulation capture threshold by a scaling factor that is obtained using an equal energy assumption for the first and second vectors.

12. The method of claim 11, wherein the estimating includes scaling the first electrostimulation capture threshold by a scaling factor that is substantially proportional to a square root of a ratio of the second impedance to the first impedance.

13. The method of claim 12, wherein the scaling factor is substantially proportional to a square root of a ratio of an electrostimulation duration used with the first vector between first and second electrodes to an electrostimulation duration to be used with the second vector between the first and third electrodes.

14. The method of claim 12, wherein the measuring the first electrostimulation capture threshold corresponding to the first vector between the first and second electrodes comprises taking the first vector between the first electrode located in association with a first heart chamber of a heart and the second electrode located elsewhere.

15. The method of claim 14, comprising taking the first vector using at least one of a second electrode located in association with a heart chamber across a septal region of the heart from the first electrode or a second electrode located in the body and outside of and not touching the heart.

16. The method of claim 12, comprising taking the second vector between the first electrode and the third electrode, wherein the third electrode is located in association with the first heart chamber of the heart.

17. The method of claim 16, wherein the first and third electrodes are located intravascularly in association with the left ventricle of the heart.

18. The method of claim 12, wherein the first electrode is configured as a cathode for delivering an electrostimulation for measuring a first electrostimulation capture threshold corresponding to the first vector.

19. The method of claim 12, wherein the first electrode is also configured as a cathode for delivering an electrostimulation, using the second vector, exceeding the estimated second electrostimulation capture threshold.

20. An apparatus comprising:

a capture threshold circuit, configured to measure a first electrostimulation capture threshold corresponding to a first vector having a first pulsewidth between first and second electrodes, wherein the first electrode is located in association with a first heart chamber of a heart and the second electrode is located elsewhere;

an impedance determination circuit, configured to determine at least a first impedance associated with the first vector between the first and second electrodes and a second impedance associated with a second vector having a second pulsewidth between the first electrode and a further third electrode, wherein the third electrode is located in association with the first heart chamber of the heart, and wherein the second pulsewidth is different from the first pulsewidth;

a processor circuit, configured to estimate a second electrostimulation capture threshold corresponding to the second vector between the first electrode and the further third electrode, the estimating including scaling the first electrostimulation capture threshold by a scaling factor that is substantially proportional to a square root of a ratio of the second impedance to the first impedance and also substantially proportional to a square root of a ratio of an electrostimulation duration, used with the first vector between first and second electrodes, and an electrostimulation duration, to be used with the second vector between the first and third electrodes;

wherein the first and third electrodes are located intravascularly in association with a left ventricle of a heart; and wherein the first electrode is configured as a cathode for delivering an electrostimulation for measuring a first electrostimulation capture threshold corresponding to the first vector, and wherein the first electrode is also configured as a cathode for delivering an electrostimulation, using the second vector, exceeding the estimated second electrostimulation capture threshold.

\* \* \* \* \*